United States Patent [19]

Schoenholz et al.

[11] 4,115,293

[45] Sep. 19, 1978

[54] DENTURE CLEANSER

[75] Inventors: Daniel Schoenholz, Basking Ridge, N.J.; Martin M. Perl, Brooklyn, N.Y.

[73] Assignee: E. I. Du Pont de Nemours and Company, Wilmington, Del.

[21] Appl. No.: 785,576

[22] Filed: Apr. 7, 1977

Related U.S. Application Data

[63] Continuation-in-part of Ser. No. 620,102, Oct. 6, 1975, abandoned.

[51] Int. Cl.² .................. C11D 3/395; C11D 7/54
[52] U.S. Cl. .................................. 252/102; 252/95;
252/103; 252/105; 252/546; 252/156; 252/550;
252/558; 252/188; 252/DIG. 2
[58] Field of Search ........................... 252/94–105,
252/188, 546, 156, 550, 558, DIG. 2

[56] References Cited

U.S. PATENT DOCUMENTS

| 2,498,343 | 2/1950 | Rider et al. | 252/103 |
| 3,171,752 | 3/1965 | Rankin | 106/194 |
| 3,434,796 | 3/1969 | Columbo et al. | 252/104 X |
| 3,518,343 | 6/1970 | Welsh et al. | 424/44 |
| 3,607,759 | 9/1971 | Barth | 252/95 X |
| 3,706,670 | 12/1972 | Gray | 252/95 |
| 3,741,901 | 6/1973 | Ziffer | 252/89 |
| 3,873,696 | 3/1975 | Randeri et al. | 252/188 X |

OTHER PUBLICATIONS

Krezanoski, "Contact Lens Products", Journal of the American Pharmaceutical Association, vol. NS10, #1, Jan. 1970, p. 16.

Primary Examiner—George F. Lesmes
Assistant Examiner—Bruce H. Hess

[57] ABSTRACT

An improved denture cleanser composition comprising a thermogenic combination of oxidizing and reducing agents in conjunction with bleaching, pH adjustment, wetting and sequestering agents.

12 Claims, No Drawings

DENTURE CLEANSER

CROSS-REFERENCE TO RELATED APPLICATIONS

This application is a continuation in part of our pending application Ser. No. 620,102, filed Oct. 6, 1975, now abandoned.

BACKGROUND OF THE INVENTION

1. Field of the Invention

This invention relates to novel denture cleansing compositions that contain oxidizing and reducing agents which combine in a thermogenic reaction.

2. Description of the Prior Art

Denture cleansers are well known in the art. For example, U.S. Pat. No. 3,488,288 discloses a powder of particulate solid mixtures dispersible in water, and containing an activating agent and peroxy oxygen-liberating matter for evolving gas bubbles. Amino-carboxylic acids and derivatives such as ethylenediamine tetraacetic acid compounded with heavy metals and ion exchange resins compounded with catalytically active metals are disclosed as the activating agents. U.S. Pat. No. 2,931,776 discloses denture cleansing compositions in a dry solid form which on addition to water produce a lively effervescence caused by the liberation of oxygen from the alkali metal perborate present in the composition. The dentures are soaked in the resulting solution which has an alkaline pH after which the dentures are rinsed with water.

SUMMARY OF THE INVENTION

In accordance with the invention, novel denture cleansing compositions have been discovered which comprise, in addition to bleaching agents, surfactants and sequestering agents, a combination of an oxidizing agent and a reducing agent which results in a thermogenic reaction; that is, a reaction which generates heat when contacted with water, thereby providing improved cleansing action.

In particular, the invention is directed to a thermogenic denture cleansing composition comprising (a) 60 to 85 wt % of a mixture of
  (1) an oxidizing agent selected from the group consisting of alkali metal percarbonate, perborate, persulfate, perpyrophosphate and monopersulfate, and
  (2) a reducing agent selected from alkali metal sulfite, thiosulfite or metabisulfite; thiourea; and ascorbic acid, (b) 5 to 15 wt % of a bleaching agent selected from the group consisting of alkali metal monopersulfates, (c) 0.01% to 5.0 wt % of a wetting agent selected from alkali metal salts of long chain alkyl sulfates, alkali metal salts of alkyl benzene sulfonates and nonionic surfactants that are stable to oxidants at a pH of 7 to 10, (d) 0.01% to 0.5 wt % of a sequestering agent selected from alkali metal salts of aminocarboxylic acids, and (e) sufficient pH adjusting agent to give the composition, when in aqueous solution, a pH of 7-10.

The composition is dry blended in powder or granular form. For convenience it may be compressed into tablets, in which case a small amount of binder such as polyvinyl pyrrolidone may be used.

In the present invention the oxidizing and reducing agents combine in a thermogenic reaction. The advantages obtained from this reaction include:

(a) better cleaning results from higher bath temperatures;
(b) more rapid solubility;
(c) greater effervescence.

The preferred oxidizing agents are sodium percarbonate and potassium percarbonate, most preferably sodium percarbonate. The preferred reducing agent is selected from the group consisting of sodium sulfite, sodium metabisulfite and thiourea, while the most preferred is sodium sulfite.

The oxidizing and reducing agents comprise 60 to 85 wt % of the composition, preferably about 68 to 73 wt % of the composition. The oxidizing and reducing agents are preferably present in approximately stoichiometric amounts. An excess of reducing agent is not recommended as it might react with the bleaching agent, thereby reducing the cleansing action of the bleaching agent. An excess of oxidizing agent is not harmful to the reaction, but it is not economically attractive. In order to insure a significant amount of heat generation, the amount of reducing agent should be from about 50 to 100% of the theoretical amount required to react stoichiometrically with the oxidizing agent and preferably at least 90%.

Wetting agents act as emulsifiers in lifting off soil. Representative examples of a wetting agent include "Nacconol NR"[1] (sodium dodecyl benzene sulfonate), "Duponol C"[2] (sodium salts of sulfated alcohols) such as "Triton X-100"[1] (water soluble iso-octyl phenoxy polyethoxy ethanol), "Dowfax 9N9"[2] (nonyl phenol-ethylene oxide condensate having 9 to 10 moles of ethylene oxide), sodium lauryl sulfate, polysorbate 80, glyceryl monostearate and sodium cetyl sulfate. The wetting agent is included in proportions below that at which a foam or scum builds up when the composition is mixed with water. Suitable concentrations of the wetting agent are from 0.01 to 5.0 wt % with a preferred concentration of 0.5 to 1.5 wt %.

(1) Manufactured by Allied Chemical Corp., National Aniline Division
(2) Manufactured by E. I. du Pont de Nemours & Co.
(1) Manufactured by Rohm & Haas Co.
(2) Manufactured by The Dow Chemical Co.

Sequestering agents are added as water conditioners and particularly to prevent a reaction between monopersulfate and manganese, which is frequently found in tap water, which results in a stain. The preferred sequestering agents are selected from ethylenediamine tetraacetic acid, diethylene triamine pentaacetic acid, sodium tripolyphosphate and metaphosphate. Ethylenediamine tetraacetic acid or diethylene triamine pentaacetic acid are most preferred. Suitable concentrations of the sequestering agent are from 0.01 to 0.5 wt % with a preferred concentration of 0.05 to 0.15 wt %.

Sufficient pH adjusting agent is added to the composition to give a resulting aqueous solution a pH of 7 to 10. Acid solutions are not recommended because they tend to etch the dentures. Alkaline solutions have the disadvantage of hastening the corrosion of metal parts of the dentures. Therefore, neutral solutions are preferred although slightly alkaline solutions may be tolerated because of improved cleaning in alkaline solutions. Suitable acidulants are tartaric, citric and ascorbic acid. Suitable bases are anhydrous sodium carbonate and sodium phosphate. Based primarily on economic factors, the preferred pH adjusting agent is tartaric acid or anhydrous sodium carbonate.

In the following examples of the present invention powdered ingredients of the composition were dry blended and compressed into tablets weighing six grams and having a diameter of 1⅜ inches. Compression pressures of approximately 5000 to 6000 psig were used. The denture plastic specimens were prepared in a steel mold designed to make a 5 inch × 5 inch × 3/16 inch plate with corrugations on one side resembling teeth. Material used was standard "Lucitone" denture acrylic obtained from L. D. Caulk Company of Milford, Delaware. The charge used for molding each plate was as follows:

"Lucitone" acrylic resin (clear): 71 g
Titanium dioxide: 3 g
"Lucitone" liquid (methyl methacrylate monomer): 30 ml The materials above were blended in a 4 oz screw capped jar and allowed to polymerize for approximately 10 to 15 minutes until a non-sticky mass was obtained. The material was then transferred to the mold and allowed to cure for 45 minutes in a heated press (220° F) under 10,000 pounds pressure. The specimens were removed after cooling and the surface cleaned and sanded with fine emery paper (Mesh Grade 280) to a smooth finish. The plate specimens were then cut into 1 inch × 1 inch squares.

The above prepared specimens were soiled with tobacco, coffee and laboratory grown dental plaque as follows:

Coffee

A staining solution prepared by adding 4 to 5 teaspoons of instant coffee (Nescafe$^{(1)}$) to approximately 250 cc of water. The specimens were placed in the solution and heated on a hot plate for about 6 to 8 hours at temperatures of 180° to 200° F. They were removed overnight and put in an oven at 80° C to set the stain. This procedure was repeated until a significant visible stain was obtained.
(1) Manufactured by The Nestle Company, Inc.

Tobacco

Tobacco tar was collected from two cartons of Philip Morris, king size "Commander" cigarettes using a "Philip Morris Automated Smoking Machine" manufactured by Phipps and Bird, Inc. of Richmond, Virginia. The tar was collected on 1¾ inch fibre glass filters (No. CM 113A Cambridge Filter Co.). The tar was then extracted from the filters with a Soxhlet apparatus using acetone as the solvent. Twelve grams of extracted tobacco tar were dissolved in approximately 250 ml of acetone. The stains were applied by placing the specimens on a warm hot plate (approximately 100° to 150° F) and brushing on the tar/acetone solution. This procedure permitted even spreading of the tar and rapid evaporation of the acetone. The specimens were dried overnight in an oven at 60° C to set the stains.

Dental Plaque

Simulated dental plaque was grown on the specimens according to laboratory procedure described below:

Each specimen was placed in a 2 oz wide-mouth jar and immersed in a plaque-forming solution, and then put in a Brunswick Shaker-Incubator set at 37° C and shaken for 6 to 8 hours. This procedure was repeated for 5 to 7 days until a significant plaque film formed. Specimens were dried overnight in between runs to help set the film. The plaque solution mentioned above consists of saliva collected from 10 to 20 subjects, a mineralizing solution, sucrose, gastric mucin and a bacterial culture of Leptotrichia buccalis.

The soiled specimens were divided into groups of three and assigned to each test so that they were equally matched according to degree of stain.

Since plaque accumulations are relatively colorless, it is necessary in order to see "soil" buildup that a suitable protein dye be used. FD&C Red No. 3 (Erythrosine) is an example of such a dye used by the dental profession. An example of a commercial consumer product is Butler "Red Kote".

The invention is further illustrated by the examples that follow in which all percentages are by weight unless otherwise designated.

EXAMPLE 1

The powdered ingredients indicated below were mixed and formed into tablets 6.0 grams in weight and 1⅜ inches in diameter containing the percentage composition indicated:

| Function | Component | % by Weight | |
|---|---|---|---|
| Bleaching | Oxone ® potassium monopersulfate* | 10.89 | (0.11 × 10$^{-2}$ mols) |
| Oxidizing | Perdox ® sodium percarbonate** | 32.43 | |
| Reducing | Sodium sulfite (anhydrous) | 39.25 | (1.87 × 10$^{-2}$ mols) |
| Wetting | Sodium lauryl sulfate | 1.09 | |
| Sequestering | Disodium salt of ethylene diamine tetraacetic acid | 0.10 | |
| Acidifying | Tartaric acid | 16.24 | |
| | Total | 100.00 | |

*Oxone ® is a triple salt of potassium monopersulfate, potassium bisulfate and potassium sulfate of formula $2KHSO_5 \cdot KHSO_4 \cdot K_2SO_4$, manufactured by E. I. du Pont de Nemours & Co.
**Perdox ® is sodium percarbonate (theoretical formula $2Na_2CO_3 \cdot 3H_2O_2$), manufactured by E. I. du Pont de Nemours & Co. In this example, the Perdox ® contained only 1.85 × 10$^{-2}$ mols of $H_2O_2$.

The oxidizing and reducing agents are present in approximately stoichiometric amounts.

A 6.0 gram tablet of the above formulation is added to approximately 125 ml of water at 115° to 120° F in a 4 oz glass jar containing a tobacco stained denture plastic specimen. A temperature increase of 14.0°–15.0° F is observed within the first minute. After 15 minutes of soaking, the specimen is removed from the 4 oz jar and rinsed under tap water. The specimen is visually evaluated for stain removal. In the case of plaque soils, the specimens are restained with a protein dye (Erythrosine) prior to the evaluation. The specimen is given ratings of from 1 to 5 based on the degree of removal of the stain. A rating of 5 indicated the complete disappearance of the stain. The specimen is placed back into the 4 oz jar and allowed to soak approximately 12 hours and then reevaluated. The above procedure is repeated with a coffee stained specimen and a dental plaque stained specimen. The results are summarized below:

| | Initially | After 15 Minutes | After 12 Hours |
|---|---|---|---|
| Tobacco | 1 | 4 | 4 |
| Coffee | 1 | 4 | 4 |
| Dental Plaque | 1 | 3 | 3 |

EXAMPLE 2

The procedure described in Example 1 was followed except that 0.74% by weight of polyvinyl pyrrolidone was used as a tablet binder to give the following composition:

| Function | Component | % by Weight | |
|---|---|---|---|
| Bleaching | Oxone ® potassium monopersulfate | 10.78 | (0.1 × $10^{-2}$ mols) |
| Oxidizing | Perdox ® sodium percarbonate | 32.33 | * |
| Reducing | Sodium sulfite (anhydrous) | 38.80 | (1.85 × $10^{-2}$ mols) |
| Wetting | Sodium lauryl sulfate | 1.08 | |
| Sequestering | Disodium salt of ethylene diamine tetraacetic acid | 0.10 | |
| Acidifying | Tartaric acid | 16.17 | |
| Binding | Polyvinyl pyrrolidone | 0.74 | |
| | Total | 100.00 | |

*Mols of $H_2O_2$ = 1.85 × $10^{-2}$.

The mol ratio of oxidizing agent to reducing agent in the formulation was about 1.06:1. Thus, the oxidizing and reducing agents are present in approximately stoichiometric amounts.

The cleaning procedure described in Example 1 was carried out and the results are summarized below:

| Stain | Initially | After 15 Minutes | After 12 Hours |
|---|---|---|---|
| Tobacco | 1 | 4 | 4 |
| Coffee | 1 | 4 | 4 |
| Dental Plaque | 1 | 3 | 3 |

COMPARATIVE EXAMPLE

A commercially available 3.2 gram tablet of "Efferdent" manufactured by Warner-Lambert Co. was subjected to the test described in Example 1 and designated Sample A. This same test was repeated with a 3.2 gram tablet of commercially available "Polident" designated Sample B manufactured by Block Drug Co. The results are summarized below:

| | Initially | | After 15 Minutes | | After 12 Hours | |
|---|---|---|---|---|---|---|
| Stain | A | B | A | B | A | B |
| Tobacco | 1 | 1 | 2 | 2 | 2 | 2 |
| Coffee | 1 | 1 | 1 | 2 | 1 | 2 |
| Dental Plaque | 1 | 1 | 1 | 1 | 1 | 1 |

In the examples above the difference between the 6 grams of the compositions of this invention and 3.2 grams of the above commercial preparations is in the additional oxidizing and reducing agents of the present invention. The bleaching agent in the composition of the invention supplies approximately the same level of active oxygen as in the above commercial preparations.

What is claimed is:
1. A thermogenic denture cleansing composition in powder or granular form comprising
   (a) 60 to 85 wt % of an approximately stoichiometric mixture of
      (1) an oxidizing agent selected from the group consisting of alkali metal percarbonate, perborate, persulfate, perpyrophosphate and monopersulfate, and
      (2) a reducing agent selected from alkali metal sulfite, thiosulfite or metabisulfite; thiourea; and ascorbic acid,
   (b) 5 to 15 wt % of a bleaching agent selected from the group consisting of alkali metal monopersulfates, said 5 to 15 wt % of alkali metal monopersulfates being in addition to any alkali metal monopersulfate used as an oxidizing agent,
   (c) 0.01% to 5.0 wt % of a wetting agent selected from alkali metal salts of long chain alkyl sulfates, alkali metal salts of alkyl benzene sulfonates and nonionic surfactants that are stable to oxidants at a pH of 7 to 10,
   (d) 0.01% to 0.5 wt % of a sequestering agent selected from alkali metal salts of aminocarboxylic acids, and
   (e) sufficient pH adjusting agent to give the composition, when in aqueous solution, a pH of 7-10.
2. The composition of claim 1 wherein the bleaching agent is potassium monopersulfate.
3. The composition of claim 1 wherein the oxidizing agent is sodium or potassium percarbonate.
4. The composition of claim 1 wherein the reducing agent is selected from sodium sulfite, sodium metabisulfite and thiourea.
5. The composition of claim 1 wherein the oxidizing agent is selected from sodium percarbonate or potassium percarbonate and the bleaching agent is potassium monopersulfate and the reducing agent is selected from sodium sulfite, sodium metabisulfite and thiourea.
6. The composition of claim 1 wherein the oxidizing and reducing agents are 70% by weight of the composition.
7. The composition of claim 1 wherein the oxidizing and reducing agents are present in approximately stoichiometric amounts.
8. The composition of claim 1 wherein a binder is incorporated.
9. The composition of claim 8 wherein the binder is polyvinyl pyrrolidone.
10. The composition of claim 1 wherein the sequestering agent is ethylenediamine tetraacetic acid.
11. The composition of claim 1 wherein the sequestering agent is diethylene triamine pentaacetic acid.
12. The method comprising soaking dentures in an aqueous solution of the composition of claim 1.

* * * * *